United States Patent
Thomet et al.

(10) Patent No.: US 9,928,421 B2
(45) Date of Patent: Mar. 27, 2018

(54) METHOD FOR HELPING DETERMINE THE VISION PARAMETERS OF A SUBJECT

(71) Applicant: INTERACTIF VISUEL SYSTEME (I V S), Clichy (FR)

(72) Inventors: Pascal Thomet, Paris (FR); David Encaoua, Carrieres sur Seine (FR)

(73) Assignee: INTERACTIF VISUEL SYSTEME (I V S), Clichy (FR)

( * ) Notice: Subject to any disclaimer, the term of this patent is extended or adjusted under 35 U.S.C. 154(b) by 198 days.

(21) Appl. No.: 14/431,764

(22) PCT Filed: Sep. 25, 2013

(86) PCT No.: PCT/EP2013/069923
§ 371 (c)(1),
(2) Date: Aug. 10, 2015

(87) PCT Pub. No.: WO2014/048961
PCT Pub. Date: Apr. 3, 2014

(65) Prior Publication Data
US 2015/0339511 A1    Nov. 26, 2015

(30) Foreign Application Priority Data
Sep. 26, 2012   (FR) .................................... 12 59044

(51) Int. Cl.
*G06K 9/00*      (2006.01)
*G06K 9/52*      (2006.01)
(Continued)

(52) U.S. Cl.
CPC .......... *G06K 9/0061* (2013.01); *A61B 5/0077* (2013.01); *A61B 5/103* (2013.01);
(Continued)

(58) Field of Classification Search
CPC .... G06K 9/0061; G06K 9/00268; G06K 9/52; G06T 7/73; A61B 5/0077; A61B 5/103;
(Continued)

(56) References Cited

U.S. PATENT DOCUMENTS

2006/0110008 A1*   5/2006   Vertegaal ........... G06K 9/00604
                                                                382/103
2011/0141227 A1    6/2011   Bigioi
(Continued)

FOREIGN PATENT DOCUMENTS

DE    10 2010 015 795 A1    10/2011
DE    10 2011 009 646 A1    8/2012
(Continued)

*Primary Examiner* — Mishawn Hunter
(74) *Attorney, Agent, or Firm* — Womble Bond Dickinson (US) LLP (57) ABSTRACT

The invention concerns a method for helping determine the vision parameters of a subject (100), comprising the following steps: —taking (120) two images (11, 12) from two different angles of the face of the subject by means of a camera (10), the subject (S) being in a natural distant vision position, —determining (130) the inclination of the camera (10) relative to the ground at the time when the images are taken, —deducing therefrom (140) the inclination and the direction of the face of the subject (S), characterized in that the camera is arranged outside a foveal area of the subject when the images (11, 12) are taken (120).

14 Claims, 4 Drawing Sheets

(51) Int. Cl.
    *G06T 7/00*            (2017.01)
    *G06F 17/30*          (2006.01)
    *A61B 5/103*          (2006.01)
    *G02C 13/00*          (2006.01)
    *A61B 5/00*            (2006.01)
    *G06T 7/73*            (2017.01)
    *A61B 3/14*            (2006.01)

(52) U.S. Cl.
    CPC .......... *G02C 13/003* (2013.01); *G02C 13/005* (2013.01); *G06F 17/3028* (2013.01); *G06K 9/00268* (2013.01); *G06K 9/52* (2013.01); *G06T 7/0012* (2013.01); *G06T 7/73* (2017.01); *A61B 3/145* (2013.01)

(58) Field of Classification Search
    CPC .. G02C 13/003; G02C 13/005; G06F 17/3028
    USPC .......................................................... 348/78
    See application file for complete search history.

(56) References Cited

U.S. PATENT DOCUMENTS

2011/0216160 A1*   9/2011   Martin ..................... H04N 5/89
                                                                 348/40
2012/0257162 A1* 10/2012   Encaoua .............. G02C 13/005
                                                                351/204
2013/0176404 A1*   7/2013   Tsukagoshi .......... H04N 13/007
                                                                  348/51

FOREIGN PATENT DOCUMENTS

EP          1 747 750 A1      1/2007
FR          2 836 215          8/2003
FR          2 971 861 A1      8/2012

* cited by examiner

METHOD FOR HELPING DETERMINE THE VISION PARAMETERS OF A SUBJECT

The invention relates to the analysis of the general posture of the face of a subject and taking measurements carried out by an operator, generally an optician, who proceeds with the acquisition of the necessary data so as to determine the general configuration of implantation of the corrective lenses with respect to the subject's eyes, for the purpose of personalization and optimization of the optical characteristics of the corrective lenses or of ophthalmic lenses which he must carry, as well as the mounting on frames.

Numerous systems are already known aiming to optimize the position of the lenses in a frame compared to the relative position of the pupils of the subject's eyes and of the frame. To this end, fixed or animated images of the face wearing the frame are taken by a camera, and the detection of the position of the eyes is carried out, as well as the detection of the position of the frame.

In particular, document FR 2 860 887 in the name of the applicant discloses a system wherein, based on a series of animated images of the subject's face during movement in front of a fixed camera, a reference image is determined wherein the face is best focused on the camera, so as to have the best definition of the relative position of the eyes and the frame.

In parallel, manufacturers of ophthalmic lenses are today trying to optimize the design of such lenses, particularly in the technology of so-called progressive lenses, by examining the behavior of the subject when his glance moves. For example, document FR 2 892 529 in the name of the application discloses a system including:
- a camera,
- a screen allowing the images taken by the camera to be displayed,
- an accessory capable of being worn fixedly on the face of the subject and carrying a plurality of visual markers,
- means forming visual target(s) capable of covering at least two determined positions I1, I2 with respect to the camera, and
- image analysis means capable of analyzing the position of visual markers in the images taken by the camera. The means of image analysis then deduce the position and the cap angle value in space of the accessory, and therefore of the subject's face, when he observes different regions of the means forming visual target(s), to deduce in particular information on the relative importance of the movement of the face during displacement of vision from one target to another, as well as the relative importance of the movement of the eyes.

Figure 1:
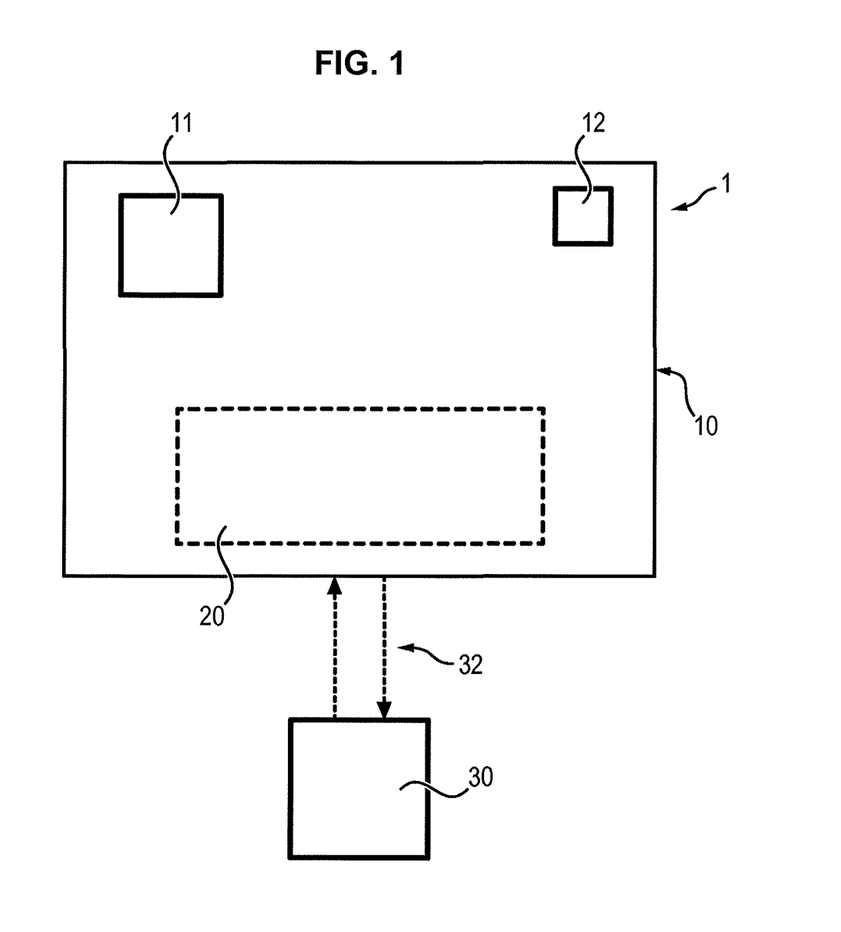
FIG. 1 is a schematic of an embodiment of a system to help in determining the parameters of vision of a subject conform to the invention.
Figure 2:
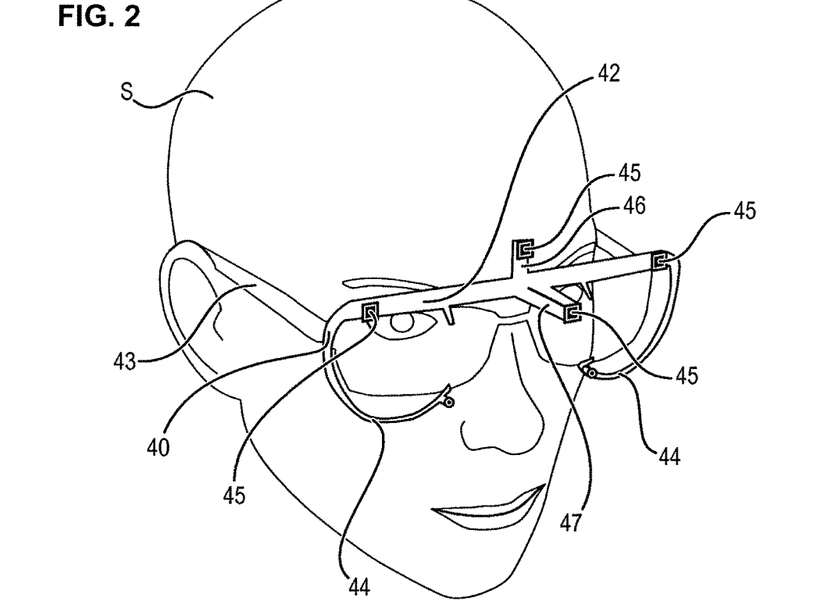
FIG. 2 is an example of an accessory which can be used with a system conform to the invention.

Typically, the accessory can conform to the accessory illustrated in FIG. 2 and include means forming geometric indicator selected specifically to highlight the orientation of the frame. It can be constituted of a rectilinear support bearing a series of visual markers, placed along the branches of the frames and/or on the superior mount of the face of the frame.

The system then makes it possible to make precise measurements of the parameters such as the position of the pupils, their spacing, etc. since the positioning of the subject and the visual markers as well as the direction of his glance (thanks to visual targets) are known and determined in space with respect to the system of measurements itself.

For the measurements to be accurate, it is also necessary that the face of the subject be in a reference posture, and watch in the position suited to taking measurement using the system.

The reference posture of the system which is concerned by the invention is the posture of distant vision, wherein the subject is held in a natural position and glances at a point at infinity straight ahead of him in a horizontal plane. As a variant, the reference posture can correspond to a close vision posture, such as the reading posture, that is the position wherein the subject glances at a point about forty centimeters from his eyes and lowers his glance by 30° compared to the horizontal plane.

The posture of the subject can for example be described (in a non-limiting manner) by means of two angles for a known glance direction.

The first angle corresponds to the cap angle value of the face, that is an oriented angle that reflects the fact that the subject has a tendency to have the face more or less turned to the left or the right when he looks at an object placed directly in front of him.

The second angle corresponds to the vertical inclination of the face, that is an oriented angle which reflects the fact that the subject has a tendency to have the face more or less raised or lowered when he is looking at an object placed directly in front of him. For a given frame, this second angle can be the measure of the pantoscopic tilt, that is the measurement of the inclination of the mean plane of the corrective lens with respect to the vertical.

In order to determine the distance between the pupils of the subject (one of the parameters for the manufacture of correction devices), the optician generally uses a pupillometer. In this case, the cap angle value is arbitrarily assumed to be zero since the pupillometer is resting against the subject's front. Nevertheless, this device does not allow taking into account the pantoscopic tilt which must be measured separately, nor, if applicable, the fact that the subject can have a way of laterally holding his head (tendency of the subject to look rather to the right or to the left in his reference position).

This approach therefore does not guarantee that the position taken by the subject corresponds correctly to his natural position. This natural position is however of great importance because it determines the manner in which the subject is going to project his glance on the lenses of the glasses in his maximum comfort position. A bad posture therefore leads to bad measures of the centering of the lenses. It is thus of primary importance to select an image where the posture is correct for calculation of the projection of the glance through the lenses of the glasses and hence to evaluate the quality of the position of the subject during measurement.

Moreover, all these systems and procedures described above do not allow the subject to watch at a distance straight ahead horizontally without having some visual hindrance, the viewing devices being placed in the visual field of the subject when he is in distant vision. Indeed, to avoid errors of perspective, the image capturing device must as close as possible to the optical axis X of the subject's glance: is therefore necessary either to place the device very far from the subject (large amount of space taken in the store and use of a camera with a powerful zoom), or to simulate a aiming point more distant from the subject than the camera. The visual targets are therefore often hindering to the user. For example, the reflection of the subject in a mirror makes it possible to double the distance between the subject and the visual target, but if the subject is nearsighted or the mirror is not sufficiently immersive (for his size or for the quality of his reflection), it can then prove difficult to focus on a precise point of the subject's face. The subject can therefore only adopt his natural distant vision posture with difficulty.

In addition, these systems are limited in space by the space available for the installation of the measurement system, so that the visual targets generally remain close to the subject, forcing him even more to constrain his glance to focus on them. Finally, these systems are bulky and require a minimum space to approximate distant vision.

Document DE 10 2010 015795 describes a device for determining the centering of a subject, including a screen, two cameras arranged on either side of the screen and a processing system. The cameras are preferably not visible by the subject, while the images selected to bring the subject to take on particular positions for measuring the vision parameters are displayed on the screen. Several parameters can be determined, including the head-eye coefficient, the center of rotation of the eye in near vision and distant vision. Nevertheless, the method described in the device impose on the person wearing it a distance that is too small, which constrains his glance and does not allow him to place himself in a natural reference posture and to look at infinity. Moreover, the system described in this document is very bulky.

Document EP 1 747 750, for its part, describes a method to establish the visual behavior of a subject, including the following steps:
provide the subject with an accessory,
have the subject be seated, facing a screen. The subject must be centered with respect to the cameras, which extend to either side of the screen, so as to obtain a stereoscopic card of the subject's face,
ask the subject to follow an image on the screen, and follow the movement of the face, and
determine the behavior of the subject based on these images.

Here again, the method requires a considerable space for its implementation and constrains the subject to fix a target set at a relatively close distance, which does not allow him to take a natural posture during measurement.

Finally, document FR 2 971 861 describes a method for determining at least one parameter of the vision of the wearer, whatever the ambient light conditions, during which the position of a calibration element of the checkerboard type is identified on an image of the head of the subject and this image is used to adjust the luminosity in the subsequent captured images. To this end, this document proposes a method during which several images are captured using a camera. The contrast is improved between each capture, thanks to calibration elements detected on the preceding image. This method therefore aims to improve the quality of the images captured by the image capturing device. It also necessitates, however a bulky system, and the images of the subject are taken facing or in profile, constraining a priori the glance of the subject during measurement.

One objective of the invention is therefore to propose a new measuring method and an associated system, allowing accurate determination the parameters of vision needed to make an eyesight correction device which does not constrain the gaze of the subject and is more polyvalent than the devices known until now, and this for moderate cost.

Here vision parameters mean in particular the parameters comprised in the following list: the pantoscopic tilt, the measurement of the pupillary distances/heights and the convergence of the eyes in this measurement, the glass-eye distance, the cap angle value, the eye-head coefficient, etc.

For this, the invention proposes a method to help the determination of parameters of the vision of a subject, including the following steps:

capturing two images at two different angles of the subject's face by means of a portable image capturing device, the subject being in a natural posture for distant vision,
determining the inclination with respect to the ground of the image capturing device at the time the images were captured,
deducing from this the pantoscopic tilt and the cap angle value of the subjects face,
wherein the image capturing device is set outside a foveal zone of the subject at the time the images were captured.

In this manner, the image capturing device does not constitute a visual hindrance in the vision field of the subject. Indeed, it no longer cuts the axis of the subject's glance, so that it is possible at present for focus on a target far away horizontally without being constrained by the space or the measuring device, and to limit the errors connected with the carriage of the head and/or to the convergence of the eyes in measuring papillary distances/heights.

Certain optional but not limiting features of the method are the following:
the image capturing device is placed, during the capture of the images. outside a zone of the subject's visual field forming a cone having an apex angle of 5° to 30° with respect to the optical axis of the subject, preferably between 15° and 25°,
one of the images is taken facing the subject, seen from below,
one of the images is taken from the side.

Such a placement of the image capturing device thus makes it possible to avoid constraining the glance and the position of the subject, by not obstructing his field of vision.
at least one of the pupils or at least one of the corneal reflections of the subject is visible on each of the captured images,
the process includes in addition a step during which the visual markers are identified in the images, the visual markers being formed on an accessory capable of being worn in a fixed manner by the face of the subject,
the image capturing device is a video camera, and the image capture step includes the following sub-steps:
film the face of the subject so as to obtain a plurality of images of the subject at different angles of view, and
select among the images of the subject at least two images at two different angles of the subject's face,
the method also comprises a step during which the visual markers in the images are identified, the visual markers being singular points of the subject's face,
the images are taken simultaneously by two image capturing devices of which the position and the cap angle value with respect to one another are known,
at the time of capture of the two images, the face of the subject is lighted,
during the step of capturing the images, a ray of light is projected onto a backing facing the subject, for example a vertical segment,
the pantoscopic tilt and the cap angle value of the subject's face are determined locally by the image capturing device, on a local computer distinct from the image capturing device, or remotely on an Internet server,
the image capturing device is a digital tablet including a video camera.

The possibility of implementing a helping method conform to the invention thus makes it possible to adopt digital tablets, which can be commercial or dedicated, to take images and for determining the vision parameters of the subject.

Other features, aims and advantages of the present invention will better appear upon reading the detailed description which will follow, made with reference to the appended figures given by way of non-limiting examples and in which.

A system 1 for aiding in the determination of vision parameters of a subject S conform to the invention includes in particular:

an image capturing device 10, configured to take images of the face of the subject S, the face of the subject including visual markers, an inclinometer, integral in motion with the image capturing device, and processing means, connected to the image capturing device and to the inclinometer.

Generally, in order to determine the vision parameters of the subject, an operator (an optician for example), takes at least two images I1, I2 of the subject at different angles thanks to the image capturing device while the subject is looking far away, so as not to hinder the subject during any of the image captures I1, I2.

To this end, the image capturing device is placed remotely from the optical axis X of the subject, preferably outside his foveal area, so as not to hinder his glance and ensure that the subject S is placed in a natural posture and is looking far away without external constraint. It is indeed important not to obstruct the foveal zone so as not to hinder the subject S. However, in order to reduce the risks of hindrance, it can be preferable to free a larger are than the foveal area. Thus, according to one embodiment, the image capturing device 10 is placed, for each of the captured images I1 and I2, outside an area of the visual field of the subject S forming a cone having an apex angle of 5° to 30° with respect to the optical axis X of each eye of the subject S, preferably between 15° and 25° (the apex of the cone being arranged on the optical axis at the face of the subject).

It will be understood indeed that, the more the image capturing device 10 is away from the optical axis X of the subject S, the less the subject will be hindered by its presence, the limit being the ability to correctly discern at least one of the pupils (or at least a corneal reflection) of the subject S.

No visual target is then imposed to subject S, so that he can adopt his natural distant vision posture. It is, however, possible for an operator to suggest such a target to the subject S, so as for example to incite subject S to look directly ahead of him. Such a target is however not part of the system 1, its position not being defined with respect to the image capturing device 10.

The images and the inclination of the image capturing device 10 are then analyzed by the processing means which deduces therefrom the vision parameters of the subject.

The Image Capturing Device 10

The image capturing device 10 can be a video camera, a photographic device, etc. The images taken by the image capturing device 10 can in particular be digital images, so as to be processed directly by the processing means.

The image capturing device 10 preferably has a wide-angle lens, so as to be able to take a complete image of the subject's face at a short distance, that is between ten centimeters and a meter. The resolution of the image capturing device 10 depends on its focal length, the distance to the person, etc., and must generally be sufficient to be able to identify visual markers 45 such as color markers or singular points in the face. For example, the resolution of the image capturing device 10 must be sufficient for an image of the eyes to include at least one pixel every 0.3 mm.

The system 1 also includes an inclinometer 20, integral in movement with the image capturing device 10, designed to determine the inclination of the image capturing device 10 with respect to a horizontal plane. Preferably, the inclinometer 20 is integral with the image capturing device 10. It can, for example, be an accelerometer coupled to an acceleration signal processing circuit. The accelerometer can also be coupled to an electronic gyroscope so as to improve the reliability of the inclinometer.

Optionally, so as in particular to measure the corneal reflection of the subject, the system 1 can also include a lighting means 12 for the face of the subject, which can be integral with the image capturing device 10.

Moreover, the image capturing device 10 can be movable and portable by an operator so as to ease its use. It can in addition include a screen 14, allowing the operator to visualize the images taken by the image capturing device 10.

Figure 3:
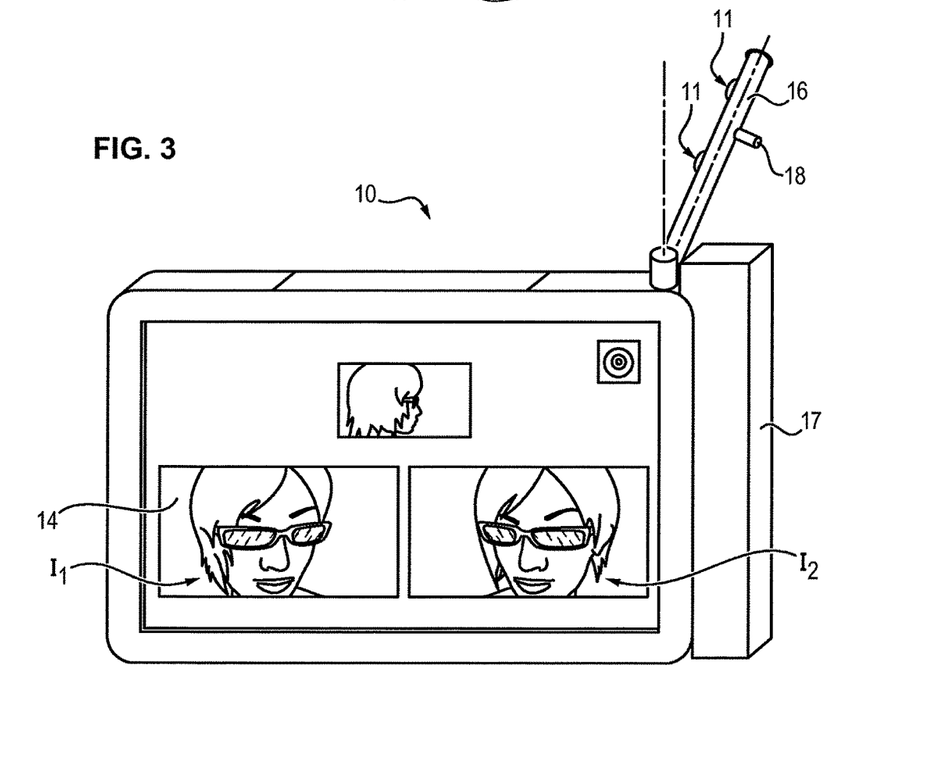
FIG. 3 is embodiment of an image capturing device which can be used in a system conform to the invention.

In the embodiment illustrated in the figures, the image capturing device 10 is for example a digital table including, in its rear face 16, a video camera 11 capable of taking images, as well as an accelerometer 20. The tablet 10 can in addition include, in its front face, a screen 14 allowing real-time visualization of the images taken by the camera 11. This can be for example of commercial tablet of the iPad® type or Galaxy Tab® type, Iphone®, a table specifically made for application to the determination of vision parameters of a subject and including an image capturing device and an adapted inclinometer, or even a smartphone.

Advantageously, the camera 11 can then be offset with respect to the geometric center of the tablet 10, being for example positioned hear one of the ends thereof, so as to facilitate the capture of images of the subject S while still remaining outside his foveal area, preferably remaining outside of an area of the field of vision forming a cone having an apex angle of 5° to 30° with respect to the optical axis X of the subject S, more preferably even between 15° and 25°, so as not to perturb his natural distant vision posture.

Optionally, the flash of the tablet 10 can be used as a lighting means 12 during image capture. The tablet 10 can however be provided with a lighting means 12 distinct from the flash and attached to it, particularly against its rear face, so as to light the face of the subject S during image capture.

Moreover, the image capturing device 10 an also include a projector 18 designed to project a visual target against a backing facing the subject S. For example, the projector 18 can be a low-power laser designed to project a luminous ray on a wall.

According to another embodiment, the image capturing device 10 can be formed by a screen 12 on which is fixed, in a removable or permanent manner, the arm 16 equipped with at least a camera 11. The arm 16 can be articulated on one of the edges of the screen 14, for example an upper edge, about an axis globally perpendicular to the edge of the screen. So as not to hinder the subject S during image capture, the arm 16 can pivot by an angle greater than 90°, for example on the order of 120°. The arm can also pivot (locally or over its entire length) about its extension axis while taking with it the camera 11, to allow easier framing the face of the subject S. For example, the arm 16 can turn about its own axis on an angle on the order of 200°.

By way of an example, the arm 16 can measure some thirty centimeters and include two cameras 11 aligned along this and separated by about ten centimeters. This embodiment then allows two photographs I1, I2 to be taken simultaneously of the face of the subject S at two different viewing angles.

In this embodiment, the arm 16 equipped with the camera(s) 11, can then be attached to a commercial tablet 10. The inclinometer 20 can then be fixed either on the tablet 10 (or integrated therewith), or on the arm 16 itself. Moreover, the attachment of the arm 16 can be carried out directly on the screen 10, or by an adapter 17 (particularly in the case where the screen is a commercial digital tablet).

Visual Markers

The visual markets can be singular points of the face, or visual markers carried by an accessory 40 worn on the face of the subject S.

The accessory 40 can in particular conform to the accessories described in documents FR 2 860 887 or FR 2 892 529, illustrated in FIG. 2. This accessory 40, made for example of a transparent plastic, includes a principal body 42 horizontally elongated with two lateral branches 43 also horizontal, extending substantially at right angles to the rear with respect to the principal body. The principal body 42 carries along its own lower edge two small clamps designed to attach along the upper edges of two lenses of eyeglasses (or on a frame) worn by the subject S, the branches 43 being also capable of holding, in a manner not illustrated, means for holding them on the branches of the frame. In this manner, as soon as the subject has put on glasses (corrective or optically neutral, or even a bare frame) in a stable position, and the accessory 40 has been put in place, said accessory occupies a well-defined position with respect to the face of the subject.

According to one aspect of the invention, the accessory can also correspond to two elastic blades 44, in metal or in plastic, which would extend from the lower edge of the principal body, and the curved form whereof is suited to come to rest against the lower edge of the lenses of the eyeglasses (or of the frame). The form of the blades 44 is also suited so that their free end follows a rectilinear trajectory, perpendicular to the principal body when they are deformed so as to be fixed onto the lenses (or the frame). In this manner, the blades 44 are always fixed on the same place on the lenses (or the frame) during measurements and do not perturb subject's glance, no matter what type of frame he has.

As illustrated in FIG. 2, the accessory 40 includes a certain number of visual markers or references 45, here eight square zones with a well-identified color, for example a bright green with a well-defined wavelength, two visual markers being situated in these well-defined spaced positions on one of the branches 43, two others arranged symmetrically on the other branch 43, 6171819202122232425262 7121cated on the principal body. More precisely, regarding these last markers, the principal body 42 of the accessory 40 includes an upwardly protruding portion 46, in the upper region whereof is found a marker 45 and a forward protruding part 47, at the free end whereof is a marker 45. The last two markers 45 are to the left and right, near the departure of the branches 43.

As a variant, the visual markers 45 can be geometric shapes such as checkerboards or even markets emitting in the infrared spectrum When the visual markers are singular points of the face, these singular points can in particular be the pupils and/or the corneal reflections, as well as points on the edges of the subject's frame.

Processing Means 30

The processing means 30 are designed to analyze the position of the visual markers in the images I1, I2 taken by the image capturing device 10 as well as the inclination of the device 10 determined by the inclinometer 20 at the time of each image capture, so as to deduce the vision parameters of the subject S.

To this end, the processing means 30 include a processor designed to collect and process the data coming from the image capturing device 10 (images I1, I2 of the face of subject S) and of the inclinometer 20 (inclination of the image capturing device 10 with respect to the ground). The results can then be displayed on the screen of the processor or, if applicable, on the screen 14 of the image capturing device 10.

The processor 30 can be incorporated directly into the image capturing device 10. This can in particular be the case when the image capturing device 10 is a digital table. All the calculations are then carried out locally on the digital tablet 10.

As a variant, the processor 30 can be a local computer distinct from the image capturing device 10, located however in proximity thereto. The image capturing device 10 then transmits the data (images and angles) to the computer through a network 32 (wireless or wired) which carries out the calculation, making it possible to obtain the parameters of the vision of the subject S. Advantageously, the system 1 can then be incorporated as a supplement to existing measurement systems, such as those described in the documents cited in the introduction to the application, and thus profit from the existing interfaces (software, management interface, etc.) which allow a reduction of the cost of development, the cost of purchasing a system when the opticians are already equipped with existing systems, and reassures the optician who already understands the equipment.

In this embodiment variant, when the image capturing device 10 is a digital tablet, the screen of the processor can be displayed on the screen 14 of the tablet 10 by an access system at a remote office, for example by an VNC (Virtual Network Computing) protocol or RDP (Remote Desktop Protocol), thus allowing the operator to manage all the operations directly from his tablet 10.

According to yet another variant, the processor 30 can be a distant internet server, which can in addition be dedicated. The images I1, I2 and the inclination of the measuring device are then transmitted (by a wireless or wired network) to the distant server 30, which sends back the results either directly to the image capturing device 10, particularly if it includes a screen 14 to display them, or to a local computer connected to the distant server.

When the visual market are formed by the singular point of the face of the subject S, the processor 30 includes means for realizing a three-dimensional reconstruction of the patient's face and to made from that reconstruction the necessary measurement to determine the vision parameters of the subject.

To that end, a triangulation for the three-dimensional reconstruction is carried out in conformity with prior art. The accessory 40 then makes it possible to know at least one known distance between two points.

As a variation, the three-dimensional reconstruction can be carried out by any other conventional photogrammetry or stereoscopy method.

In the embodiment variant implementing the singular points of the face, the system 1 includes at least two image capturing devices 10, the position and orientation in space with respect to one another are known. It is then possible to determine the position of the singular points of the face and their distance thanks to the reference images taken simultaneously with two image capturing devices 10 according to the techniques of photogrammetry and of stereoscopy describe above.

Method

We will at present describe a method for helping determine the vision parameters of a subject 100 conforming to the invention. The method 100 will be illustrated hereafter with a system 1 consisting of a digital table 10 including a screen, a video camera and an accelerometer 20. This is however non-limiting, the method 100 being implementable with all image capturing devices 10 and inclinometers 20 conforming to what was described above.

In order to accomplish these measurements, the subject S is first placed in his natural reference posture and looks away 110. For that he puts himself at ease and glances at a point at infinity straight ahead of him on a horizontal plane. This position is therefore not constrained but free, to the extent that he does not need to watch an imposed visual marker or to look into a mirror.

Figure 4A:
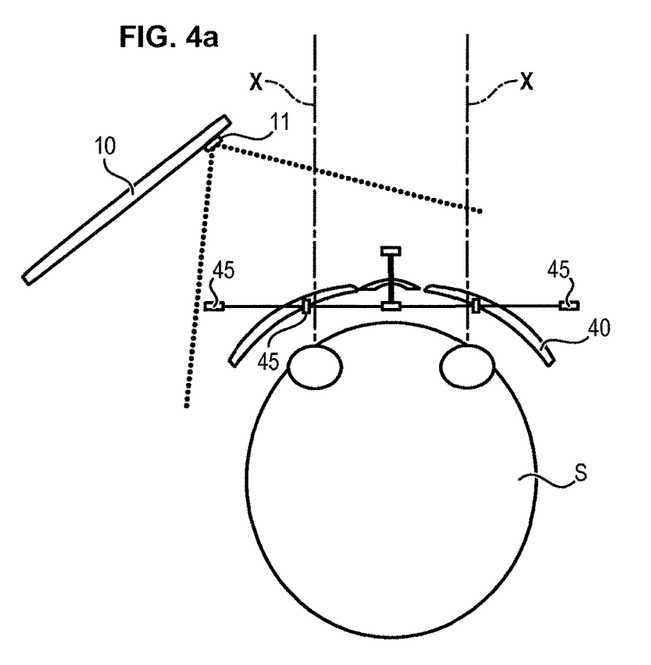
FIGS. 4a and 4b illustrate an example of image captures conform to the invention.
Figure 4B:
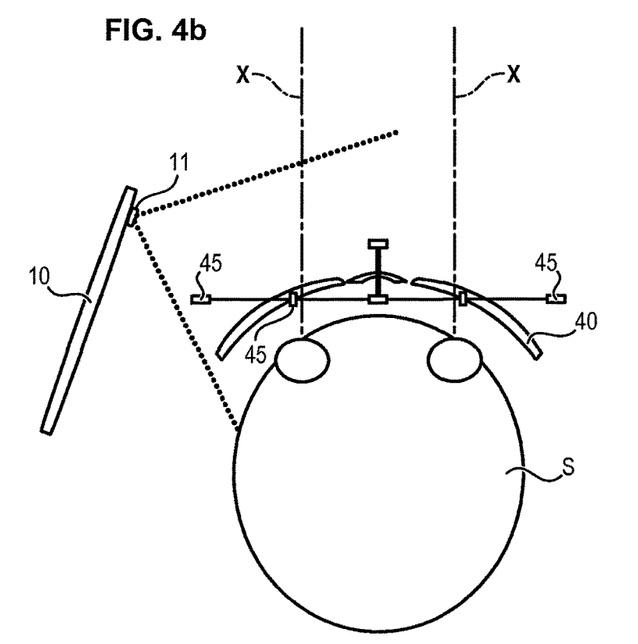

The operator then captures at least two images I1, I2 of the subject's face at a short distance 120, framing the face so that at least one of the subject's pupils is found in both images. In this manner, it is then possible to carry out measurements at least for the corresponding eye. Given the small distance between the camera 11 and the face of the subject S (between 10 centimeters and one meter), images I1, I2 are obtained having good resolution. One example of placement of the image capturing device 10 and of the video camera 11 during capture of the images I1 and I2 with respect to the face of the subject S and to his optical axis is illustrated in FIGS. 4a and 4b.

Figure 5:
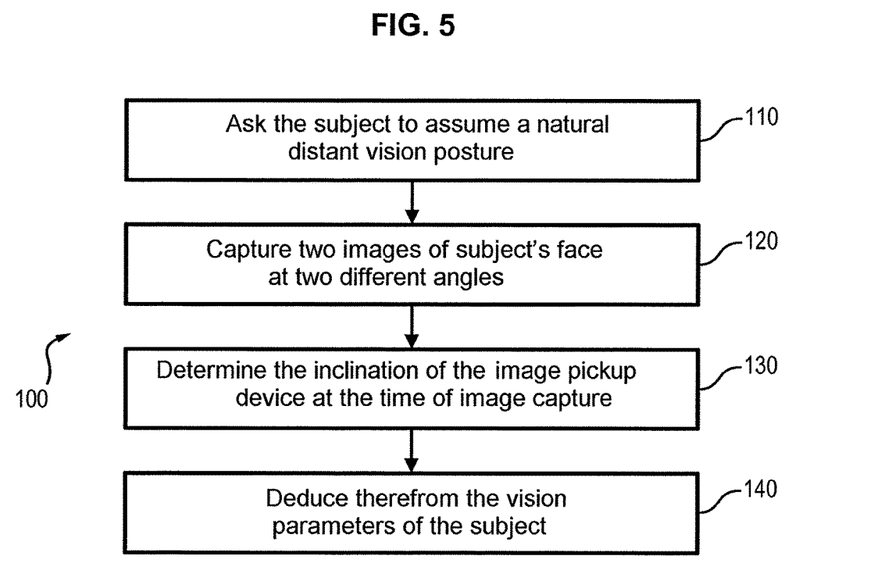
FIG. 5 is a flowchart illustrating different steps of an embodiment of a method to help in the determination of vision parameters of a subject conform to the invention.

When the image capturing device 10 is a video camera, it is possible to either take the two images I1 and I2 directly from two different viewing angles, or to film the face of the subject. The film is made in such a way as to take a plurality of different images of the image of the subject S and from different viewing angles. Two images I1 and I2, taken from different viewing angles and suitable for the method, are then selected from among this plurality of images. For example, it is possible to film the face of the subject by displacing the video camera 10 between a lateral position and a position below the face of the subject, making sure not to hinder his glance (that is, remaining way from his foveal area). This selection of images making it possible to determine the different vision parameters of the subject S.

In the case where the visual markers 45 are singular points on the face, the images I1 and I2 are taken preferably simultaneously by two distinct image capturing devices 10, the position and orientation relative to one another are known.

Optionally, the lighting means 12 can be lit during the entire image capture step 120, or simply at the time of each image capture. In the case where the visual markers are markers 45 placed on an accessory, the lighting means 12 can be positioned on the accessory 40 itself rather than on the tablet 10, so as to light the pupils of the subject S.

If need be, the operator can use the screen 14 of the tablet to help correctly frame the image of the subject S.

For example, the operator takes an image I1 from in front seen from below so as not to penetrate into the field of vision of the subject S, and therefore not to perturb his natural distant vision posture, and an image I2 from the side, at an angle less than 90° so that the two pupils are visible (for example, a three-quarters view).

As a variant, the operator can take two images I1, I2 from the side of the face at different angles, for example at 20° and at 40° from the viewing axis of the subject S, so as not to perturb his field of vision. These images I1, I2 can be obtained in succession by displacing the tablet 10 between the two image captures I1, I2, or simultaneously while the tablet 10 is equipped with the arm 16 equipped with two cameras 11 spaced apart.

During these measurements, the images I1, I2 are then registered by the digital tablet 10, while the accelerometer 20 determines the inclination of the tablet 10 at the time of each image capture 130.

The images I1, I2 and the inclination of the tablet 10 are then transmitted to the processor 30, so as to determine the respective position of the various visual markers in the two images I1, I2 and to deduce therefrom the natural pantoscopic tilt and the natural cap angle value of the subject's face 140, as well as the vision parameters such as the convergence of the subject S.

The determination of the visual markets can be made automatically by the processor 30 itself, or manually by the operator.

A digital tablet 10 being generally tactile, the operator can in particular visualize and point to visual markers directly on the images I1, I2 displayed on the screen 14. It can thus determine the position of the irises, the pupils, by applying principles of photogrammetry and of stereoscopy. This information is then used by the processor 30 to deduce therefrom the convergence of the subject S.

Optionally, when the face of the subject is lit thanks to the lighting means 12, the processor 30 can also determine the convergence of the subject S from his corneal reflections and from the position of the irises using conventional calculation methods.

These results can then be displayed on the screen 14 of the tablet or of a computer positioned nearby.

In order to improve the measurement of the subject's natural cap angle value, it is possible to project a visual target, preferably a vertical segment, onto a support such as a wall, by means of a project 18 fixed to the tablet 10, and to ask the patient to look at this target at the time of image capture. In this manner, the subject is forced to place his head in the position corresponding to a zero cap angle value.

The visual target can be a vertical segment so as not to perturb the measurement of the pantoscopic tilt of the subject's face.

The invention claimed is:

1. A method for helping determine the vision parameters of a subject (100), including the following steps:
    capture (120) a first image (I1, I2) at a first angle of the subject's face by means of an image capturing device (10) and a second image at a second angle of the subject's face by means of the image capturing device, the second angle being different from the first angle and the subject (S) being in a natural distant vision posture,
    determine (130) the inclination of the image capturing device with respect to the ground at the time of image capture,
    deduce therefrom (140) the vision parameters of the face of the subject (S), characterized in that the image capturing device is positioned outside a foveal area of the subject at the time of capture (120) of the images (I1, I2).

2. The method according to claim 1, wherein the image capturing device (10) is placed during image capture (120) outside an area of the field of vision of the subject (S), said area forming a cone having an apex angle of 5° to 30° with respect to an optical axis (X) of the subject (S), preferably between 15° and 25°.

3. The method according to claim 1, wherein one of the images (I2) is taken in front of the subject, from below.

4. The method according to claim 1, wherein one of the images (I2) is taken from the side.

5. The method according to claim 1, wherein at least one of the pupils or at least one of the corneal reflections of the subject (S) is visible on each of the captured images (I1, I2).

6. The method according to claim 1, further including a step during which visual markers (45) are identified in the images, the visual markers (45) being formed on an accessory (40) which is worn fixedly on the face of the subject (S).

7. The method according to claim 1, wherein the image capturing device (-20) is a video camera, and the step of capturing images includes the following sub-steps:
 filming the subject's face so as to obtain a plurality of images at different viewing angles, and
 choosing among the images of the subject at least two images (I1, I2) at two different angles of the subject's (S) face.

8. The method according to claim 1, further including a step during which visual markers (45) are identified in the images, the visual markers (45) being singular points of the subject's (S) face.

9. The method according to claim 8, wherein the images (I2) and (I2) are taken simultaneously by two image capturing devices (10), the position and the relative orientation of said image capturing devices being known.

10. The method according to claim 1, wherein at the moment of capture of the two images (I1, I2), the face of the subject (S) is lit.

11. The method according to claim 1, wherein, during the step consisting of capturing the images (I1, I2), a beam of light is projected onto a support which faces the subject (S), for example a vertical segment.

12. The method according to claim 1, wherein the pantoscopic tilt and the cap angle value of the subject's face (S) are determined locally by the image capturing device, on a local computer distinct from the image capturing device, or remotely on an Internet server.

13. The method according to claim 1, wherein the image capturing device (10) is a digital tablet including a video camera (11).

14. The method of claim 1 wherein the vision parameters comprise at least one of the following parameters: a pantoscopic tilt, a measurement of the pupillary distances, a measurement of the pupillary heights, a convergence of the eyes in these measurements, a glass-eye distance, a cap angle value, an eye-head coefficient.

* * * * *